United States Patent [19]

Appel et al.

[11] Patent Number: 5,256,440
[45] Date of Patent: Oct. 26, 1993

[54] PROCESS FOR PRODUCING A TABLET CORE APERTURE

[75] Inventors: Leah E. Appel; Gaylen M. Zentner, both of Lawrence, Kans.

[73] Assignee: Merck & Co., Inc., Rahway, N.J.

[21] Appl. No.: 902,187

[22] Filed: Jun. 22, 1992

[51] Int. Cl.$^5$ ............................ A61K 9/44; B05D 3/00
[52] U.S. Cl. ......................................... 427/3; 427/275; 427/467; 427/480
[58] Field of Search .............. 424/467, 480; D24/103; 427/3, 275

[56] References Cited

U.S. PATENT DOCUMENTS

| | | | |
|---|---|---|---|
| 3,851,648 | 12/1974 | Brooke | 424/467 |
| 4,218,433 | 8/1980 | Kooichi et al. | 427/3 |
| 4,271,113 | 6/1981 | Luschen | 264/112 |
| 4,713,248 | 12/1987 | Kjornaes et al. | D24/103 |
| 4,792,448 | 12/1988 | Ranade | 424/467 |
| 4,865,849 | 9/1989 | Conte et al. | 427/3 |
| 5,002,775 | 3/1991 | Toya et al. | 424/467 |
| 5,110,598 | 5/1992 | Kwan et al. | 427/3 |

FOREIGN PATENT DOCUMENTS

| | | | |
|---|---|---|---|
| 1178853 | 12/1984 | Canada | 427/3 |
| 0060023 | 9/1982 | European Pat. Off. | 427/3 |
| 1372040 | 10/1974 | United Kingdom | 424/467 |

OTHER PUBLICATIONS

R. C. Rowe, et al., "The Effect of Intagliation Shape on the Incidence of Bridging on Film-Coated Tablets", J. Pharm. Pharmacol. 33, 412 (1981).
R. C. Rowe, et al., "Bridging of the Intagliations on Film Coated Tablets", J. Pharm. Pharmacol, 34, 282 (1982).
R. C. Rowe, et al., "The Effect of Plasticizer Type and Concentration on the Incidence of Bridging of Intagliations on Film-Coated Tablets", J. Pharm. Pharmacol. 33, 174–175 (1981).
R. C. Rowe, et al. "The Effect of Film Thickness on the Incidence of the Defect Bridging of Intagliations on Film Coated Tablets", J. Pharm. Pharmacol, 32, 647–648 (1980).
R. C. Rowe, et al., "The Effect of Polymer Molecular Weight on the Incidence of Film Cracking and Spliting on Film Coated Tablets", J. Pharm. Pharmacol, 32, 583 (1980).
A. G. Hansson, et al., "Perforated Coated Tablets for Controlled Release of Drugs at a Constant Rate", J. Pharm. Science, 77, 322–324, (1988). (Apr.).

*Primary Examiner*—Terry J. Owens
*Assistant Examiner*—Erma Cameron
*Attorney, Agent, or Firm*—Francis P. Bigley; Joseph F. DiPrima

[57] ABSTRACT

Process for preparing and film coating a dosage form. An intagliated dosage form core is produced by inscribing one or more areas on the surface of the dosage form core prior to coating. An aqueous dispersion of a polymeric coating is then applied to the intagliated dosage form core. When placed in an environment of use, the film coating within the circumscribed region of the dosage form surface is reproducibly expelled, leaving a coated core tablet with a predefined aperture in the coating which exposes a discrete portion of the core surface to the environment of use.

17 Claims, 3 Drawing Sheets

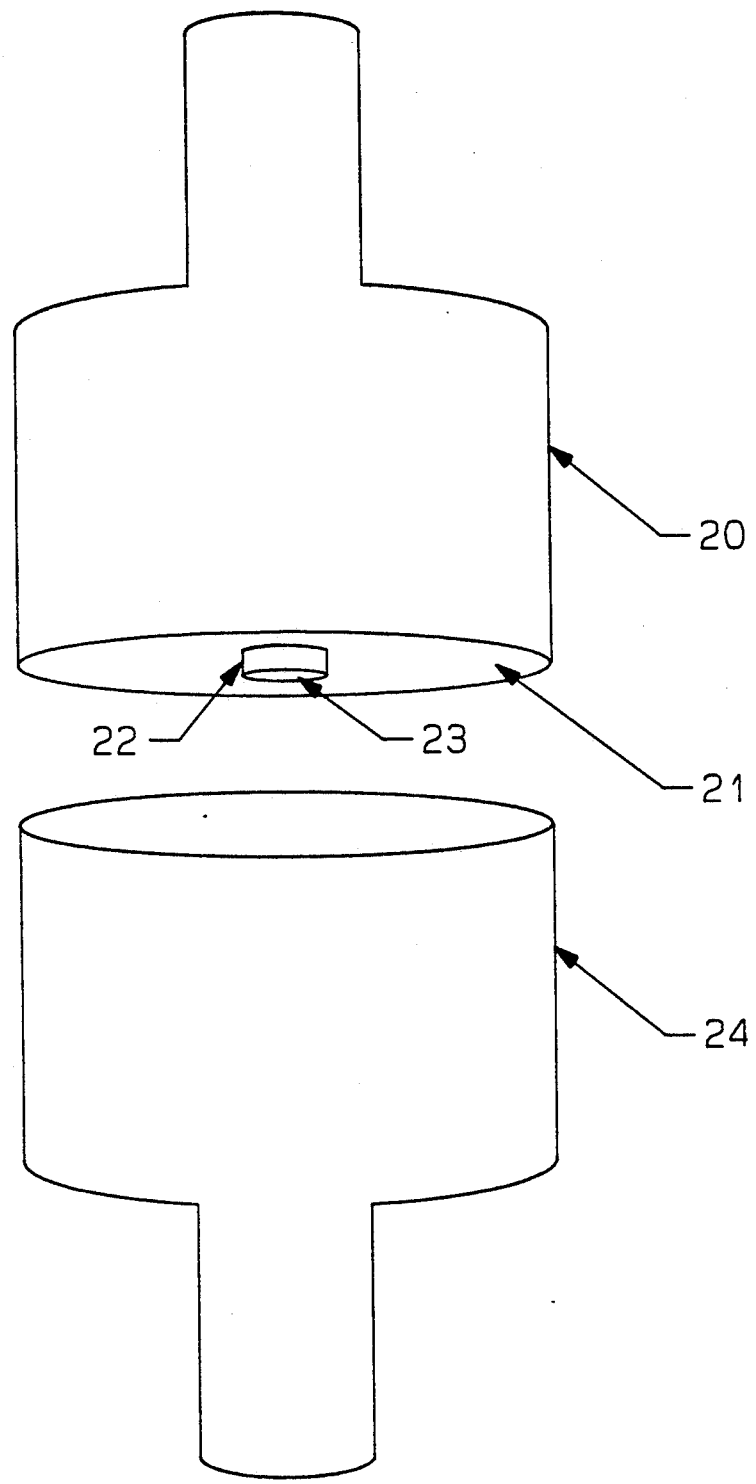

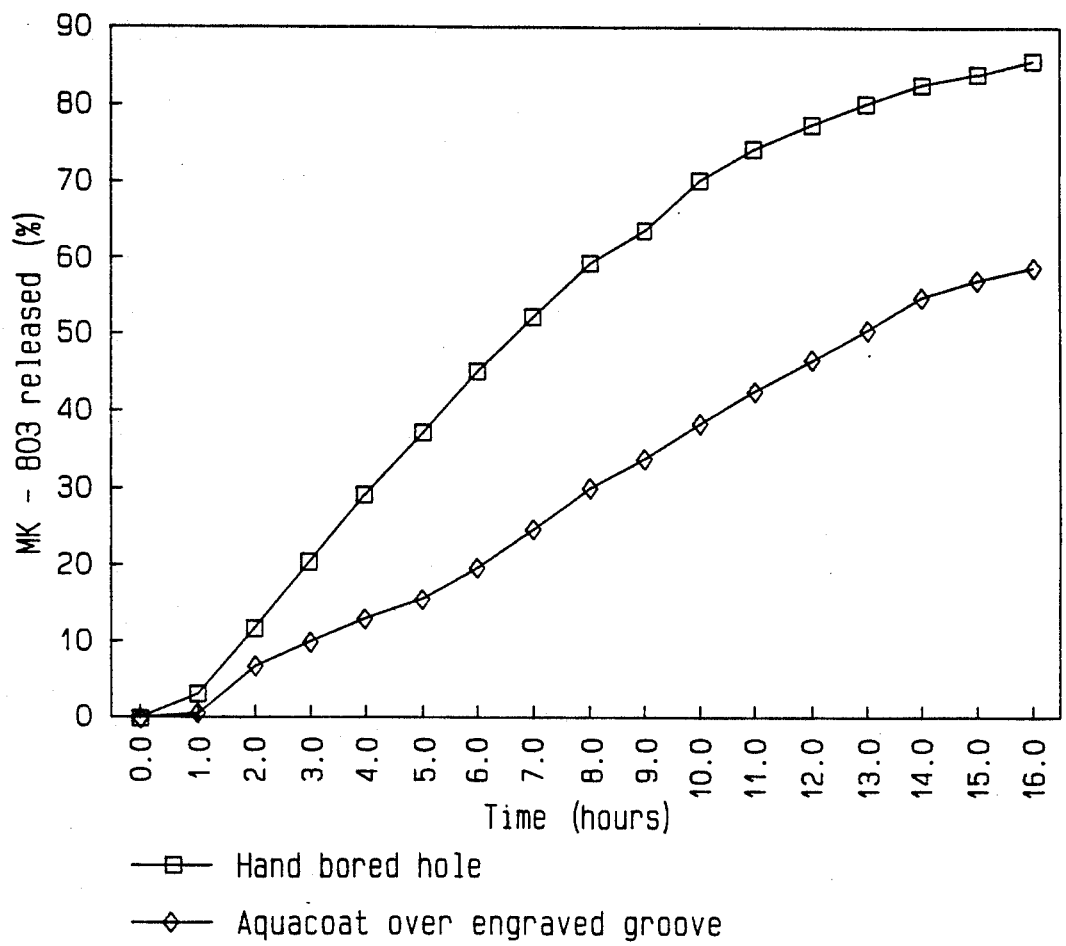

PROCESS FOR PRODUCING A TABLET CORE APERTURE

FIELD OF THE INVENTION

This invention pertains to both a novel and useful process for preparing and coating dosage forms in a manner which results in permanent application of a polymeric coating to certain areas of the dosage form surface while assuring removal of predefined portions of the coating from other portions of the surface, once the dosage form is in an environment of use.

Prior to coating, a groove is inscribed into the uncoated dosage form surface. The groove circumscribes the area on the face of the dosage form which is to be exposed during use. The intagliated dosage form core which results is then film coated with a polymeric aqueous dispersion. The relatively large size of the spray droplets appears to affect the manner in which the circumscribed area is coated. Examination of the coated tablets reveals that the coating, once applied to the dosage form, is quite thick (50-200 um) on the surface of the tablet but becomes thin or non-existent in the groove. Once in an aqueous environment, the film coating within this circumscribed area detaches and the predefined underlying area of the core is exposed, allowing hydration of the core and subsequent drug release to the environment of use.

BACKGROUND OF THE INVENTION

The need for a coating process which permits application of dosage form coating material on a batch scale yet ultimately results in the exposition of predefined portions of the coated object is well established.

In the pharmaceutical industry, there is a need for a solid dosage form coating process capable of applying a water insoluble and poorly water permeable coating onto a solid dosage form which allows for exposure of predefined portions of the dosage form to the environment of use.

Pending U.S. application Ser. No. 07/815,304, filed Dec. 28, 1991, relies on the discrete application of a coating to predetermined portions of the solid dosage form, to assure proper delivery of medicament over an extended period of time. This coating can be applied manually so as to assure that a particular surface is uncoated or alternatively, the entire tablet can be coated and then drilled to provide a hole through the film coating to expose the surface of the dosage form. Both of these techniques are time consuming, expensive and not amenable to batch processing of tablets.

A procedure to form a passageway in a film coating is taught in U.S. Pat. No. 4,271,113. This patent describes a process for forming an outlet passageway in an osmotic dispensing device by compressing a pin point recess or indentation in the core tablet and then spray coating the core tablet with a wall forming material. The indentation remains partially uncoated. This indentation does not result in the detachment of protective film coating during operation, rather, a permanent hole remains through the film coat after the coating operation is complete.

SUMMARY OF THE INVENTION

The invention concerns a novel process for preparing and film coating a dosage form. An intagliated dosage form core is produced by inscribing one or more areas on the surface of the dosage form core prior to coating. An aqueous dispersion of a polymeric coating, i.e., latex, is then applied to the intagliated dosage form core. When placed in an aqueous environment of use, the film coating within the circumscribed region of the dosage form surface is reproducibly detached, leaving a coated core tablet with a predefined discrete portion of the core surface exposed to the environment of use.

BRIEF DESCRIPTION OF THE DRAWINGS

FIG. 2 is a angled side view of a tableting punch designed to produce an intagliated dosage form core during a typical tablet compression manufacturing process.

FIG. 3 is a plot of the data obtained for the release of lovastatin from an intagliated dosage form core using U.S.P. dissolution method II.

DETAILED DESCRIPTION OF THE DRAWINGS

Figure 1:
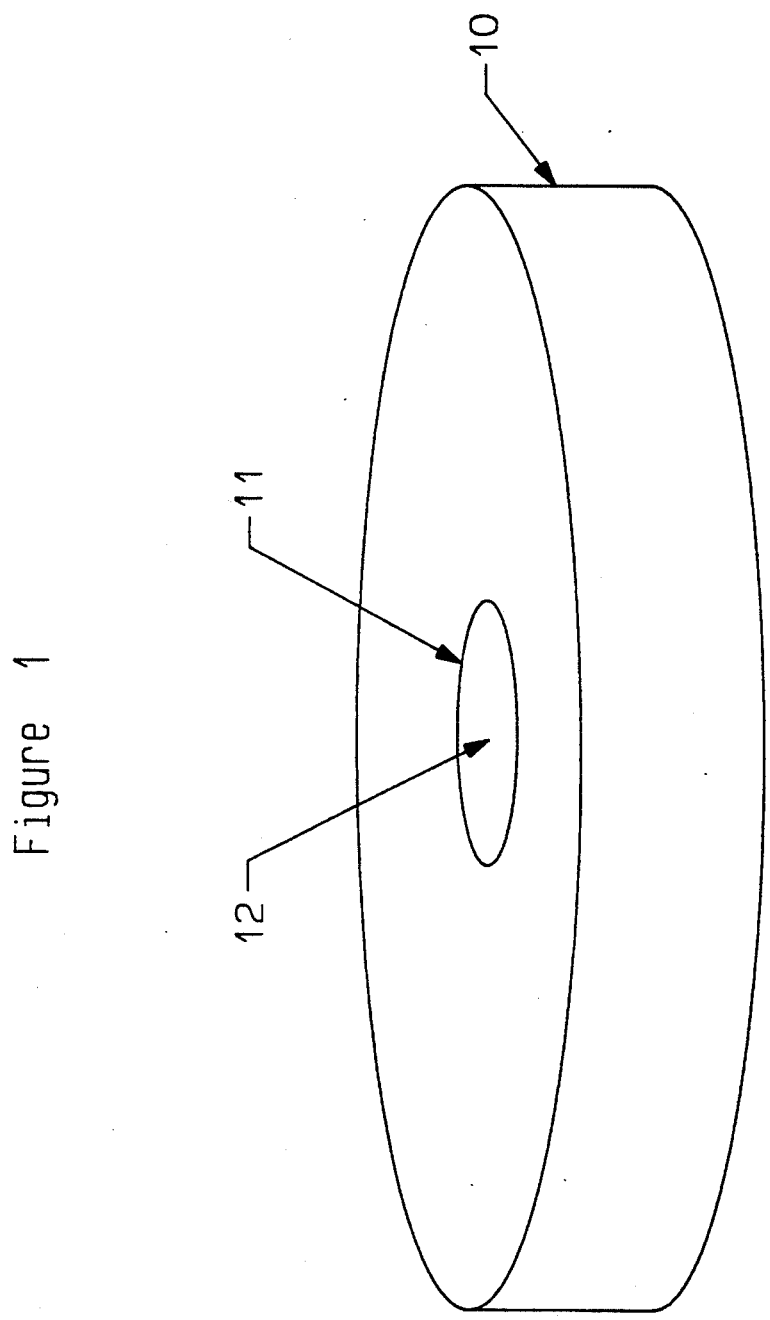
FIG. 1 is a view of an intagliated dosage form core. The area circumscribed by the groove detaches once the dosage form is placed within an aqueous environment of use.

FIG. 1 is a side view of an intagliated dosage form (10) prior to film coating. The dosage form has at least one groove (11) cut or compressed into the core which circumscribes the intended detachable coating area (12). Once in the environment of use, the area (12) circumscribed by the groove (11) detaches from the surface of the dosage form, exposing the underlying core surface.

FIG. 2 is a side view of a set of punches capable of producing a convex surface intagliated dosage form core. The upper punch (20) consists of a compressing face (21) and at least one groove producing embossed section (22) capable of producing the groove required during compressing. The embossed section (22) has a hollow interior (23) surrounded by the walls of the embossed section (22); the hollow interior (23) terminates in the same plane as the punch compressing face (21). Punch 24 can also contain an embossed section (22) if an intagliated surface is desired on both sides of a compressed dosage form or it can be a smooth surface as shown.

DESCRIPTION OF THE INVENTION

The instant invention is directed to a novel process for producing a film coated dosage form which comprises a solid or compressed core with a latex polymer film coating, the film coating comprising a detachable zone and a fixed zone, wherein the detachable zone, when exposed to an environment of use, detaches from the device to expose a portion of the surface of the compressed core beneath the detachable zone of the film coating, and the fixed zone remains attached to the compressed core, the process comprising:

(a) inscribing the surface of the dosage form core, so as to produce an intagliated dosage form having a continuous groove which defines the boundary of and circumscribes the area of the core surrounding the site of the detachable zone;

(b) formulating the latex polymer film coating;

(c) coating the intagliated dosage form core of (a) with the polymeric dispersion of (b) so that the detachment of the circumscribed coating material occurs when the dosage form is placed in the aqueous environment of use, exposing the circumscribed surface of the core.

The phrase "dosage form" includes, but is not limited to tablets, boluses, capsules, pills, disks, lozenges, controlled delivery devices and any other chemical delivery device in need of a film coating. By "chemical delivery device" is meant any device designed to deliver pharmaceutical agents, medicaments, pesticides, rodenticide, fungicides, water treatment, or other chemicals to a liquid environment.

By "polymeric film" coating is meant any polymeric material capable of forming an aqueous latex dispersion and functioning as a coating material for a dosage form. Any polymer that meets these requirements may be utilized. Cellulose esters, cellulose ethers, methacrylic and acrylate polymers and derivatives are useful in the film coating.

The phrase "detachable zone" refers to the portion of the surface of the intagliated dosage form which is to be exposed once the film coating within the circumscribed area detaches. By "intagliated dosage form" is meant a dosage form containing a continuous groove, inscribed into the surface, where the groove is continuous, that is, completely encompassing a portion of the surface.

The phrase "fixed zone" refers to the surface of the intagliated dosage form which retains its coating in the environment of use.

By "environment of use" is meant the aqueous environment into which the dosage form is placed. Commonly, this will be the gastrointestinal track of a human or other animal.

The phrase "inscribing the surface of the compressed core" refers to the introduction of a continuous groove in the surface of the dosage form core which circumscribes the surface of the dosage form core to be exposed to the medium of the environment of use. The inscription is made before the coating is applied and can be made manually by cutting a groove into the surface of the dosage form core. The groove can also be introduced by automated laser or mechanical cutting and drilling or it can be compressed directly into the dosage form core during manufacture.

The phrase "continuous groove" refers to the groove which is cut or compressed into the dosage form core. The groove is continuous in that it completely circumscribes the detachable zone, and defines its perimeter. The grooved dosage form core is referred to as an "intagliated dosage form core".

The phrase "formulating the latex film coating", refers to the formation of a aqueous dispersion of the polymer coating material prior to application to the tablets. Any of the well known techniques involved in creating a polymeric film coating or latex may be employed.

The term "latex" refers to the aqueous colloidal dispersion of natural synthetic or semi-synthetic polymers, for example: natural lattices which occur as the natural products of certain plants and trees; synthetic lattices obtained by emulsion polymerization (i.e., lattices prepared from monomers which are polymerized as an emulsion to form submicroscopic spherical polymer particles colloidally suspended in water); or artificial lattices which are colloidal dispersions of polymers prepared by direct emulsification of the bulk polymer in an aqueous medium. Such lattices are generally stabilized by surfactants.

For industrial purposes, lattices are often produced by emulsion polymerization. A monomer or mixture of monomers is emulsified in water and polymerization is induced in the aqueous phase by an initiator. Surfactants play an important role in emulsion polymerization. Their adsorption at the interface lowers the interfacial tension between the dispersed and continuous phases and surrounds the particles with a firmly bound water envelope, stabilizing the emulsion against coagulation. The adsorbed layers of amphipathic surfactants are oriented in such a way that their hydrophilic polar heads are pointing into the continuous phase while the hydrophobic non-polar tails are anchored in the dispersed phase.

Other classes of polymers and resins such as the cellulosics used in the instant invention which can not be produced as lattices by emulsion polymerization may be prepared in latex form by post emulsification of the presynthesized polymer. Surfactants also play an important role in stabilization of lattices made by these methods.

The dispersion may be applied to the intagliated dosage form core using any coating procedure including the use of a fluidized bed film coating device, a pan coater or a baffled pan coater or any air suspension process.

The novel process of the instant invention may be used to produce dosage forms used for the delivery of pharmaceutical agents. The term "animal" includes mammals, humans and primates, such as domestic, household, sport or farm animals such as dogs, sheep, goats, cattle, horses and pigs, laboratory animals such as mice, rats and guinea pigs, fish, avians, reptiles and zoo animals.

The pharmaceutical agents that can be delivered by the novel device of this invention, include inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine and hormone systems, immunological system, reproductive system, skeletal systems, autocoid systems, alimentary and excretory systems, inhibitory and histamine systems, and those materials that act on the Examples of beneficial medicaments are disclosed in *Remington's Pharmaceutical Sciences,* 16th Ed., 1980, published by Mack Publishing Co., Eaton, Pa.; and in *The Pharmacological Basis of Therapeutics,* by Goodman and Gilman, 6th Ed., 1980, published by the MacMillan Company, London; and in *The Merck Index,* 11th Edition, 1989, published by Merck & Co., Rahway, N.J. The medicament can be in various forms, such as charged molecules, charged molecular complexes or ionizable salts. Acceptable salts include, but are not limited to hydrochlorides, hydrobromide, sulfate, laurylate, palmitate, phosphate, nitrate, borate, acetate, maleate, malate, succinate, tromethamine, tartrate, oleate, salicylate, salts of metals, and amines or organic cations, for example quaternary ammonium.

Additionally, where appropriate, the medicament may be incorporated into the backbone of a polymer or may be incorporated into the backbone of the charged resin used in the formulation to effect spheronization.

Derivatives of drugs such as esters, ethers and amides without regard to their ionization and solubility characteristics can be used alone or mixed with other drugs. Also, a drug can be used in a form that upon release from the device, is converted by enzymes, hydrolyzed by body pH or other metabolic processes to the parent form, or to a biologically active form.

Specific examples of medicaments which may be adapted for use include, barbiturates such as pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and α-bromoisovaleryl urea; hypnotic and sedative urethanes and disulfanes; psychic energizers such as isocarboxazid, nialamide, imipramine, amitryptyline hydrochloride, pargylene, and protryptyline hydrochloride; tranquilizers such as chloropromazine, promazine, fluphenzaine, reserpine, deserpidine, and meprobamate; benzodiazepines such as diazepam and chlordiazepoxide; anticonvulsants such as primidone, phenytoin, and ethosuximide; muscle relaxants and antiparkinson agents such as mephenesin, methocarbomal, cyclobenzaprine hydrochloride, trihexylphenidyl hydrochloride, levodopa/carbidopa, and biperiden; antihypertensives such as α-methyldopa and the pivaloyloxyethyl ester of α-methyldopa; calcium channel blockers such as nifedipine, diltiazem hydrochloride, diltiazem malate and verapamil hydrochloride; angiotensin converting inhibitors such as enalapril and captopril; analgesics such as morphine sulfate, codeine sulfate, meperidine, and nalorphine; antipyretics and antiinflammatory agents such as aspirin, indomethacin, ibuprofen, sodium indomethacin trihydrate, salicylamide, naproxen, colchicine, fenoprofen, sulindac, diflunisal, diclofenac, indoprofen and sodium salicylamide; local anesthetics such as procaine, lidocaine, tetracaine and dibucaine; antispasmodics and muscle contractants such as atropine, scopolamine, methscopolamine, oxyphenonium, papaverine; prostaglandins such as $PGE_1$, $PGE_2$, $PGF_{2\alpha}$; antimicrobials and antiparasitic agents such as penicillin, tetracycline, oxytetracycline, chlorotetracycline, chloramphenicol, thiabendazole, ivermectin, and sulfonamides; antimalarials such as 4-aminoquinolines, 8-amino-quinolines and pyrimethamine; hormonal and steroidal agents such as dexamethasone, prednisolone, cortisone, cortisol and triamcinolone; androgenic steroids such as methyltestosterone; estrogenic steroids such as 17α-estradiol, α-estradiol, β-estradiol, estriol, α-estradiol 3-benzoate, and 17-ethynyl estradiol-3-methyl ether; progestational steroids such as progesterone; sympathomimetic drugs such as epinephrine, phenylpropanolaminehydrochloride,amphetamine,ephedrine and norepinephrine; hypotensive drugs such as hydralazine; cardiovascular drugs such as procainamide hydrochloride, amyl nitrite, nitroglycerin, dipyridamole, sodium nitrate and mannitol nitrate; diuretics such as chlorothiazide, acetazolamide, methazolamide, hydrochlorothiazide, amiloride hydrochloride and flumethiazide, sodium ethacrynate, and furosemide; antiparasitics such as bephenium, hydroxynaphthoate, dichlorophen and dapsone; antineoplastics such as mechlorethamine, uracil mustard, 5-fluorouracil, 6-thioguanine and procarbazine; β-blockers such as pindolol, propranolol, metoprolol, oxprenolol, timolol maleate, atenolol; hypoglycemic drugs such as insulin, isophane insulin, protamine zinc insulin suspension, globin zinc insulin, extended insulin zinc suspension, tolbutamide, acetohexamide, tolazamide and chlorpropamide; antiulcer drugs such as cimetidine, ranitidine, famotidine and omeprazole; nutritional agents such as ascorbic acid, niacin, nicotinamide, folic acid, choline, biotin, pantothenic acid; essential amino acids; essential fats; ophthalmic drugs such as timolol maleate, pilocarpine nitrate, pilocarpine hydrochloride, atropine sulfate, scopolamine; electrolytes such as calcium gluconate, calcium lactate, potassium chloride, potassium sulfate, sodium fluoride, ferrous lactate, ferrous gluconate, ferrous sulfate, ferrous fumurate and sodium lactate; and drugs that act on α-adrenergic receptors such as clonidine hydrochloride; analgesic drugs such as acetaminophen, oxycodone, hydrocodone, and propoxyphene; antihypercholesterolemic drugs such as simvastatin, pravastatin, lovastatin and gemfibrozil; antiinfective drugs such as cefoxitin, cefazolin, cefotaxime, ciprofloxacin, cephalexin, norfloxacin, amprolium, ampicillin, amoxicillin, cefaclor, erythromycin, nitrofurantoin, minocycline, doxycycline, cefadroxil, miconazole, clotrimazole, phenazopyridine, clorsulon, fludalanine, pentizidone, cilastin, phosphonomycin, imipenem; gastrointestinal drugs such as bethanechol, clidinium, dicyclomine, meclizine, prochlorperizine, trimethobenzamide, loperamide, diphenoxylate, and metoclopramide; anticoagulant drugs such as warfarin, phenindione, and anisindione; and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine,pseudoephedrine,alendronate, finasteride, trimethoprim, and ivermectin.

The above list of medicaments is not meant to be exhaustive. Many other medicaments will certainly work in the instant invention.

By "therapeutically effective amount" is meant that the quantity of beneficial agent, contained in the core, which can be delivered to the environment of use, has been demonstrated to be sufficient to induce the desired biological effect.

Other excipients such as lactose, magnesium stearate, microcrystalline cellulose, starch, stearic acid, calcium phosphate, glycerol monostearate, sucrose, polyvinylpyrrolidone, gelatin, methylcellulose, sodium carboxymethylcellulose, sorbitol, mannitol, polyethylene glycol and other ingredients commonly utilized as stabilizing agents or to aid in the production of tablets may also be present in the dosage form core.

The presently preferred swellable polymer materials are hydrogels that swell in, and retain a significant amount of, water. Polymeric hydrogels (which can be crosslinked or uncrosslinked) swell or expand significantly in water, usually exhibiting a 2 to 50 fold or greater volume increase. The crosslinked polymers will swell and will not dissolve; uncrosslinked polymers may dissolve subsequent to swelling although dissolution is not a necessary consequence. Examples of swellable polymers include: crosslinked polymethacrylate and polyacrylate polymers derivatized with hydroxyalkyl and/or ionizable acidic or basic functional groups, and their respective salt forms; crosslinked polyvinylpyrrolidone; crosslinked polyvinyl alcohols; poly(ethylene oxide)s; polymethacrylamides and polyacrylamides; derivatized or modified cellulosic polymers such as crosslinked sodium carboxymethylcellulose, crosslinked hydroxypropylcellulose, starch graft copolymers, crosslinked hydroxypropylmethylcellulose, crosslinked dextrans and agarose, and microcrystalline cellulose; carboxymethylamide; and polyelectrolytes.

The process described herein is further applicable to the production of slow or controlled release dosage forms capable of delivering chemicals to the environment of use at a prescribed rate for short or long periods of time.

The detachable zone of the film coating may be any shape. In general, a chord across the widest point of the release zone will range in length from about 0.5 mm to about 5 mm. However, smaller and larger dimensions are provided for in this procedure.

In general the film coating may be applied to any thickness desired. However, a coating of from about 50 to about 200 um is generally applied to the surface of the intagliated dosage form core. This coating generally appears thin or non-existent in the continuous groove.

The depth of the groove ranges from about 0.3 mm to about 1.0 mm. The depth of the groove is not necessarily the same throughout the perimeter. The width of the groove ranges from about 0.3 mm to about 0.7 mm. The width of the groove is not necessarily the same throughout the perimeter. Both the width and depth are chosen so that the spray particles droplets of the coating dispersion do not readily move into the groove.

As previously stated, inscription of the surface of the compressed core can be accomplished using mechanical as well as laser means. One such mechanical means involves compressing a tablet using a tablet punch designed to produce the intagliated surface during the compressing process. In this procedure, the punch face contains one or more embossed portions capable of incorporating one or more continuous grooves into the face or faces of a compressed dosage form.

Any number of circumscribed areas may be compressed, machined or laser drilled into the surfaces of the solid dosage form. Therefore the delivery rate of the chemical contained within the dosage form core may be regulated by producing more or fewer circumscribed areas on the core prior to coating with the polymeric dispersion.

EXAMPLES

Example 1

Intagliated dosage form cores containing lovastatin, an acrylic acid polymer (CARBOPOL 934P), trisodium citrate and lactose in a 5:2:4:2 ratio were used to study the coating technique. Circular grooves were cut into the dosage form cores. The width of the grooves ranged from about 0.3 mm to about 0.7 mm and the depth of the groove ranged from about 0.3 mm to about 1.0 mm. Chords across the widest points of the circumscribed release zone were about 3 mm.

The coating formulation was prepared as follows: 250 mL of a commercial ethylcellulose latex (AQUACOAT®; 75 g solids) was placed in a beaker and magnetically stirred. The plasticizer, dibutyl sebacate (DBS), was slowly added over a period of 1-2 minutes to a final concentration based on the amount of solids in the latex dispersion (36 g DBS /100 g AQUACOAT® solids).

Coatings were applied to the intagliated dosage form cores in a side vented pan coater. Coating conditions were as follows: inlet air temperature=80° C., air flow pressure=1.2 kg/cm², coating spray rate=1 ml/min, pan speed=25 rpm. After coating to about 100 um thickness, the coated dosage forms were cured at 60° C. for 16 hours.

Drug release studies were performed in a standard U.S.P. dissolution method II apparatus in 900 mL of phosphate buffer (isotonic; pH 7.4, 0.05 M phosphate with 0.4% SDS), at 37° C. with constant stirring at 50 rpm. Lovastatin release was monitored by ultra violet detection at 247 nm.

A representative release profile of lovastatin is shown in FIG. 3, demonstrating controlled release of lovastatin from the dosage form. The AQUACOAT® coated intagliated dosage form cores showed spontaneous detachment of the coating circumscribed by the circular groove once introduced into the aqueous buffer. Microscopic examination of coated devices before exposure to water revealed that the coating had not coated the walls of the groove evenly. There was a relatively thick coat at the top of the groove, but at the bottom of the groove little coating was observed.

Example 2

Intagliated dosage forms are prepared as in example 1. The coating formulation is prepared as follows: 250 ml cellulose acetate latex obtained from FMC Corporation (75 g solids), is placed in a beaker and magnetically stirred, 250 ml of water is added. The plasticizer, diacetin, is slowly added over a period of two minutes to a final concentration based on the amount of solids in the latex dispersion (100% g/g cellulose acetate latex solids). Coatings are applied as described in example 1.

Example 3

Intagliated dosage forms are prepared as in example 1. The coating formulation is prepared as follows: 200 ml of EUDRAGIT® RS-300 is sieved through a 190 35 sieve then placed in a beaker and magnetically stirred. Nine (9) grams of plasticizer, 15% acetyltributylcitrate, is added. Coatings are applied as in example 1.

We claim:

1. A process for producing a film coated dosage form, which comprises a dosage form core with a polymeric latex film coating, the film coating comprising a detachable zone and a fixed zone, wherein the detachable zone, when exposed to an environment of use, detaches from the dosage form to expose a portion of the surface of the dosage form core beneath the detachable zone of the film coating, and the fixed zone remains attached to the dosage form core, the process comprising:
   (a) inscribing the surface of the dosage form core, so as to produce an intagliated dosage form core having a continuous groove which defines the boundary of and circumscribes the area of the core surrounding the site of the detachable zone;
   (b) formulating the polymeric latex film coating; and
   (c) coating the intagliated dosage form core of (a) with a latex polymeric dispersion of (b) so that the detachment of the circumscribed coating material occurs when the dosage form is placed in an environment of use, exposing the underlying surface of the dosage form core.

2. The process of claim 1 wherein the film coated dosage form comprises pharmaceutical dosage forms used in the delivery of medicament to human and non-human animals.

3. The process of claim 2 wherein the pharmaceutical dosage form is a slow release drug delivery device.

4. The process of claim 1 wherein a chord measured across the widest point of the detachable zone ranges in length from about 0.5 mm to about 5 mm.

5. The process of claim 1 wherein the detachable zone of the film coating is irregularly shaped.

6. The process of claim 1 wherein the continuous groove in the surface of the dosage form core is produced manually, mechanically or with a laser.

7. The process of claim 6 wherein the continuous groove of the surface of the dosage form is produced during compression of the drug dosage form core.

8. The process of claim 7 wherein the continuous groove of the surface of the dosage form is produced using a tablet punch comprising a raised or embossed design on the face of the tablet punch as the core is compressed.

9. The process of claim 1 wherein the continuous groove has a width of from about 0.3 mm to about 0.7 mm and the depth ranges from about 0.3 mm to about 1.0 mm.

10. The process of claim 9 wherein the latex film coating is selected from the group consisting of cellulose ether, cellulose ester, cellulose acetate, methacrylate polymers and acrylate polymers.

11. The process of claim 10 wherein the latex film coating is an ethyl cellulose latex.

12. The process of claim 11 wherein the ethyl cellulose latex is mixed with dibutyl sebacate in water to a final concentration of about 36 g dibutyl sebacate/100 g of ethyl cellulose solids.

13. The process of claim 1 wherein the coating is carried out using a batch film coating process.

14. The process of claim 13 wherein the batch film coating process is performed using a fluidized bed film coating device.

15. The process of claim 13 wherein the batch film coating process is performed using a pan coater.

16. The process of claim 13 wherein the batch film coating process is performed using an air suspension process.

17. A process for film coating a pharmaceutical dosage form for the controlled in situ production and release of a suspension containing a pharmaceutical agent, consisting essentially of:
 (a) compressing a tablet core which comprises
  i. a therapeutically effective amount of a pharmaceutical agent; and
  ii. a polymer which upon hydration forms gelatinous microscopic particles;
 (b) inscribing the surface of the tablet core so as to produce a continuous trough which circumscribes and defines the boundary of an area on the tablet core surface which is to be exposed once the dosage form is placed into an aqueous environment;
 (c) thereafter film coating the tablet core with an aqueous latex which in final form is impermeable to and insoluble in water, wherein the film coating outside the inscribed area remains attached to the surface of the tablet core and the film coating inside the inscribed area detaches from the surface of the tablet core once the dosage form enters an aqueous environment.

* * * * *